Feb. 16, 1954 G. MERRILL Plant Pat. 1,256
NECTARINE TREE
Filed Jan. 12, 1953
Fig. 1
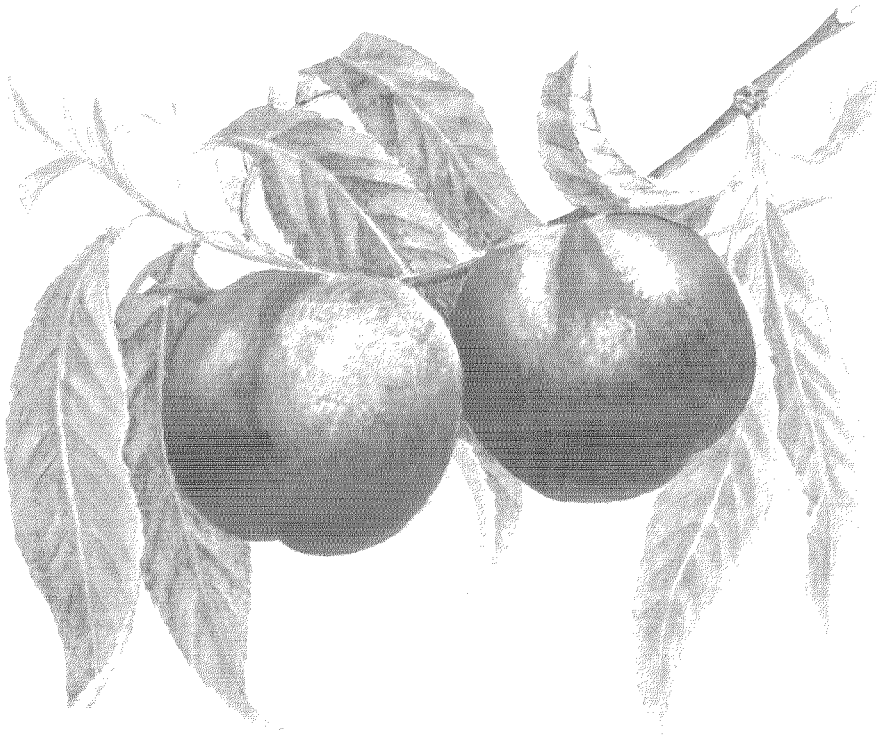
Fig. 3
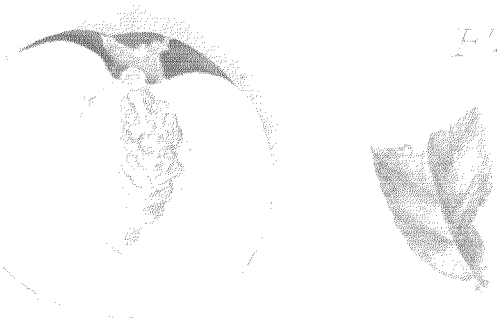
Fig. 2
WITNESS
Addison H. Avery
INVENTOR
GRANT MERRILL
Webster & Webster
ATTYS Patented Feb. 16, 1954

Plant Pat. 1,256

UNITED STATES PATENT OFFICE 1,256

NECTARINE TREE

Grant Merrill, Red Bluff, Calif.

Application January 12, 1953, Serial No. 330,932

1 Claim. (Cl. 47—62)

The present invention relates to a new and distinct variety of nectarine tree; such variety being characterized—as compared to the John Rivers (unpatented) variety of nectarine tree—by a harvest season approximately ten days earlier; and by semi-freestone fruit which is larger, more highly colored, round, and having flesh whose texture is medium, firm, and crisp.

The instant variety of nectarine tree bears fruit, therefore, for market use which is available to the trade a substantial number of days ahead of the fruit of the John Rivers variety of nectarine; the latter heretofore having been the earliest commercial nectarine.

Additionally, the fruit of the herein claimed variety of nectarine tree has good shipping quality and very good keeping quality.

The present variety of nectarine tree was originated by me upon my ranch near Red Bluff, California, in the following manner:

A cross was made between the J. H. Hale (unpatented) peach and the Flaming Gold (unpatented) nectarine, and of the resulting peach seedlings one of them was selected as being a superior variety. Seeds of this selected variety—open pollenated—were then planted, and among the resulting seedlings one was the present variety of nectarine, which was recognized as new and distinct and selected for subsequent propagation.

Subsequently, the present variety was successfully asexually reproduced by June buds on Lovell (unpatented) peach seedlings and also on older trees; the reproductions, upon careful observation, having been found to carry forward each and every one of the characteristics of the parent. Such reproduction of the variety was accomplished on a ranch near McFarland, California.

In the original drawings:

Fig. 1 is an elevation of fruit of the variety, together with leaves and twigs.

Fig. 2 is a sectional elevation of one of the fruit with the stone exposed.

Fig. 3 is a fragmentary elevation of a leaf.

Referring now more specifically to the pomological details of this new and distinct variety of nectarine tree, the following is an outline description thereof; all major color plate identifications being by reference to Maerz and Paul Dictionary of Color.

Tree: Medium size; medium vigor; upright; open; vasiform; very productive; regular bearer.

Trunk: Medium stockiness; medium shagginess.

Branches: Medium stockiness; medium shagginess.

*Color.*—Grey brown.

*Lenticels.*—Medium quantity; medium to large size.

Leaves: Length, 6 1/16" to 9 1/16", average 7". Width, 1 3/16" to 1 23/32", average 1 19/32". Medium size. Shape — lanceolate. Point — acuminate. Medium thickness.

*Color.*—Top side—medium green (22–L–7). Under side—lighter green (21–I–4).

*Margin.*—Finely crenate.

*Petiole.*—Medium length; medium slenderness;

*Glands.*—One to four in number, average 3. Alternate arrangement; medium size. Shape—reniform. Color—green in spring, red in fall. Position—base of leaf blade and petiole. Stipules—on new growth, dropping off early. Leaf twigs—normally medium brown, current season's growth light red on top, green on under side, as shown.

Flower buds: Large size. Length—medium to large. Shape—obtuse. Free; pubescent.

Flowers: Date of first bloom—March 4, 1952. Date of full bloom—March 14, 1952. Earliness compared with others — midseason. Size—large. Color—pink.

Fruit: Firm ripe—June 20, 1952. Soft ripe—June 25, 1952.

*Size.*—Uniform; medium. Diameter axial—average 2 1/2". Diameter transverse in suture plane—average 2 13/32".

*Form.*—Uniform; symmetrical; globose; few slightly oblate.

*Suture.*—Distinct; shallow, extending from base to beyond but discontinuous at apex, slight depression beyond pistil point.

*Ventral surface.*—Strongly rounded; lips equal on both sides.

*Cavity.*—Rounded to slightly elongated in suture plane; suture showing on one side. Breadth—5/8" to 7/8", average 3/4". Color—Greenish Yellow (21–L–7), shading to red occasionally.

*Base.*—Truncate.

*Apex.*—Depressed. Pistil point—none.

Skin: Medium thickness; medium toughness. Flavor—neutral to slightly astringent. Tendency to crack—slight in dry season. Down—none. Color—Yellow (10–L–5) under color, overlaid almost entirely with mahogany red (4–K–11, shading to 5–L–6, shading to 7–L–6).

Flesh:

*Color.*—Yellow (10–L–4), shading somewhat toward orange (10–L–6).

*Surface of pit cavity.*—Yellow.

*Amygdalin.*—Moderate.

*Juice.*—Moderate; watery.

*Texture.*—Medium; firm; crisp.

*Fibres.*—Abundant; medium coarseness; tender.

*Ripens.*—Evenly over entire surface, no tendency to ripen at any one place.

*Flavor.*—Subacid; mild.

*Aroma.*—Slightly distinct.

*Eating quality.*—Good.

Stone: Cling when firm ripe, semi-free when soft ripe.

*Fibres.*—Medium amount.

*Size.*—Medium. Length—1¼″. Breadth—⅞″. Thickness—⅝″.

*Form.*—Elliptical to slightly ovoid, cuneate to elliptical toward base, ovate toward apex.

*Base*—Slightly oblique.

*Hilum.*—Oval to oblong.

*Apex.*—Acute.

*Sides.*—Mostly equal, few slightly unequal.

*Surface.*—Regularly furrowed from apex toward ventral side, pitted toward base.

*Ridges.*—Toward ventral side, rounded toward apex.

*Ventral edge.*—Thin to medium thickness from base to beyond center, without wings.

*Dorsal edge.*—Deeply grooved throughout; continuous; thick; shallow, narrow grooves; ridges interrupted.

*Color.*—Brownish yellow (10–H–7).

*Tendency to split.*—None.

Use: Market; dessert; local; long distance shipment.

Keeping quality: Good.

Shipping quality: Good.

The tree and its fruit herein described may vary in slight detail due to climatic and soil conditions under which the variety may be grown.

Having thus described my invention, I claim:

A new and distinct variety of nectarine tree, as described and illustrated, characterized—in comparison to the John Rivers variety of nectarine—by semi-freestone fruit having a ripening period approximately ten days earlier than said John Rivers nectarine; by fruit having highly colored skin, the latter being yellow overlaid to a major extent with mahogany red; and by fruit which is relatively large size, round, and having yellow flesh whose texture is medium, firm, and crisp.

GRANT MERRILL.

No references cited.